US012778717B2

(12) United States Patent

Sterental et al.

(10) Patent No.: US 12,778,717 B2
(45) Date of Patent: *Nov. 3, 2026

(54) METHODS FOR DELIVERY OF DENTAL TREATMENT

(71) Applicant: Align Technology, Inc., San Jose, CA (US)

(72) Inventors: Rene Sterental, Palo Alto, CA (US); Lou Shuman, Chevy Chase, MD (US); Maia Singer, Campbell, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/260,164

(22) Filed: Jul. 3, 2025

(65) Prior Publication Data

US 2025/0331959 A1 Oct. 30, 2025

Related U.S. Application Data

(63) Continuation of application No. 17/079,872, filed on Oct. 26, 2020, now Pat. No. 12,357,428, which is a continuation of application No. 14/717,229, filed on May 20, 2015, now Pat. No. 10,813,721, which is a continuation of application No. 11/760,689, filed on Jun. 8, 2007, now Pat. No. 9,060,829.

(51) Int. Cl.

| | |
|---|---|
| ***A61C 7/08*** | (2006.01) |
| ***G09B 23/28*** | (2006.01) |
| ***G16H 50/20*** | (2018.01) |
| ***G16H 50/50*** | (2018.01) |
| *A61C 7/00* | (2006.01) |

(52) U.S. Cl.

CPC ................ *A61C 7/08* (2013.01); *G09B 23/28* (2013.01); *G16H 50/20* (2018.01); *G16H 50/50* (2018.01); *A61C 7/002* (2013.01)

(58) Field of Classification Search

CPC .................................. A61C 3/00; A61C 7/002

See application file for complete search history.

(56) References Cited

U.S. PATENT DOCUMENTS

| | | | | |
|---|---|---|---|---|
| 2007/0226005 A1* | 9/2007 | Smith | .................... | G16H 70/20 707/999.001 |
| 2011/0281229 A1* | 11/2011 | Abolfathi | ................. | A61C 7/00 433/24 |

* cited by examiner

*Primary Examiner* — Joseph D Burgess

(74) *Attorney, Agent, or Firm* — FisherBroyles, LLP

(57) ABSTRACT

A method for managing delivery of dental treatment may include identifying a dental treatment plan for a patient's teeth and generating one or more first treatment tasks to implement a first phase of the dental treatment plan. The method may also include obtaining a digital representation of a dentition, generating graphical treatment instructions representing how to administer the one or more first treatment tasks on the digital representation of the dentition, and prior to fabricating a first dental appliance for carrying out the dental treatment plan, graphically representing, to a treating practitioner, the graphical treatment instructions for how to administer the one or more first treatment tasks.

20 Claims, 7 Drawing Sheets

METHODS FOR DELIVERY OF DENTAL TREATMENT

CROSS-REFERENCES TO RELATED APPLICATIONS

This application is a continuation of U.S. patent application Ser. No. 17/079,872, filed on Oct. 26, 2020, which is a continuation of U.S. patent application Ser. No. 14/717,229, filed on May 20, 2015, (now U.S. Pat. No. 10,813,721, issued on Oct. 27, 2020) which is a continuation of U.S. patent application Ser. No. 11/760,689, filed Jun. 8, 2007 (now U.S. Pat. No. 9,060,829, issued on Jun. 23, 2015), the full disclosures of which are incorporated herein by reference in their entirety.

The present application is related to U.S. application Ser. No. 11/760,705, entitled "Treatment Progress Tracking And Recalibration," filed on Jun. 8, 2007 (now U.S. Pat. No. 8,562,388 issued on Oct. 22, 2013); U.S. application Ser. No. 11/760,701, entitled "Treatment Planning And Progress Tracking Systems and Methods," filed on Jun. 8, 2007 (Abandoned); and U.S. application Ser. No. 11/760,612, entitled "System And Method For Detecting Deviations During The Course Of An Orthodontic Treatment To Gradually Reposition Teeth," filed on Jun. 8, 2007 (now U.S. Pat. No. 8,075,306 issued on Dec. 13, 2011); the full disclosures of which are incorporated herein by reference in their entirety.

BACKGROUND OF THE INVENTION

The present invention relates generally to the field of orthodontics, and more particularly to systems and methods of managing delivery of an orthodontic treatment plan using treatment guidelines, instructions and appointment planning tools customized to the individual patient being treated.

An objective of orthodontics is to move a patient's teeth to positions where function and/or aesthetics are optimized. Traditionally, appliances such as braces are applied to the patient's teeth by an orthodontist and the set of braces exerts continual force on the teeth and gradually urges them toward their intended positions. Over time and with a series of clinical visits and adjustments to the braces, the orthodontist eventually adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, CA, under the tradename Invisalign® System. The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as ClinCheck® from Align Technology, Inc. The design of the aligners can rely on computer modeling of a series of planned successive tooth arrangements, and the individual aligners are designed to be worn over the teeth and elastically reposition the teeth to each of the planned tooth arrangements.

Recent advances in orthodontic treatment, including availability of the treatment systems discussed above, have made orthodontic treatment options available to a wide variety of patients and dental practitioners. Unfortunately, barriers to more wide-spread use of such treatment options still exist, thereby preventing both patients and dental practitioners from access to orthodontic treatment technology they desire. One such barrier includes more wide-spread use of orthodontic treatment technology to dental practitioners with limited experience in orthodontics. For example, many general dental practitioners with limited knowledge or exposure to orthodontics may be interested in learning orthodontic techniques and providing such treatment to patients, but may lack confidence in their abilities to effectively deliver treatment and/or achieve predictable outcomes. Accordingly, improved methods and techniques are needed for facilitating orthodontic practice among practitioners with limited experience in orthodontics and will enhance treatment options and improve efficacy in patients in need of such treatment.

BRIEF SUMMARY OF THE INVENTION

The present invention provides improved systems and methods of managing delivery of an orthodontic treatment plan using treatment guidelines, instructions and appointment planning tools customized to the individual patient being treated. The customized information provided according to the present invention can be offered in support or addition to orthodontic treatment systems currently available, and additionally provides to a treating practitioner specifically customized and tailored appointment guidelines and instructions regarding recommended patient/practitioner appointments as well as specific tasks that should be accomplished at identified appointments. Information and guidelines according to the invention techniques provides numerous advantages in that they provide more customized and specific guidelines and instructions for administering treatment and can be used, for example, to more effectively manage delivery of orthodontic treatment and increase treatment efficacy. For example, the inventive techniques more advantageously assist certain practitioners, including those that may lack experience and/or confidence in delivering orthodontic treatment or may be concerned about an ability to achieve a predictable or desired outcome in orthodontic care, as well as practitioners desiring more customized guidelines for a given treatment plan.

Thus, in one aspect, the present invention provides methods and systems of managing delivery of an orthodontic treatment plan. Such a method can include generating a treatment plan for a patient, generating a customized set of treatment guidelines, e.g., corresponding to a phase of the treatment plan, and providing the set of customized treatment guidelines as well as a set of orthodontic appliances to the practitioner. Systems for managing delivery of an orthodontic treatment plan is provided. A system can include a computer coupled to a server, the computer comprising a processor and a computer readable medium. The computer readable medium of the system can include instructions which, if executed, cause the computer to generate a treatment plan for a patient, generate a set of customized treatment guidelines, and generate digital models for each appliance of a set of orthodontic appliances for treating the patient according to the treatment plan.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
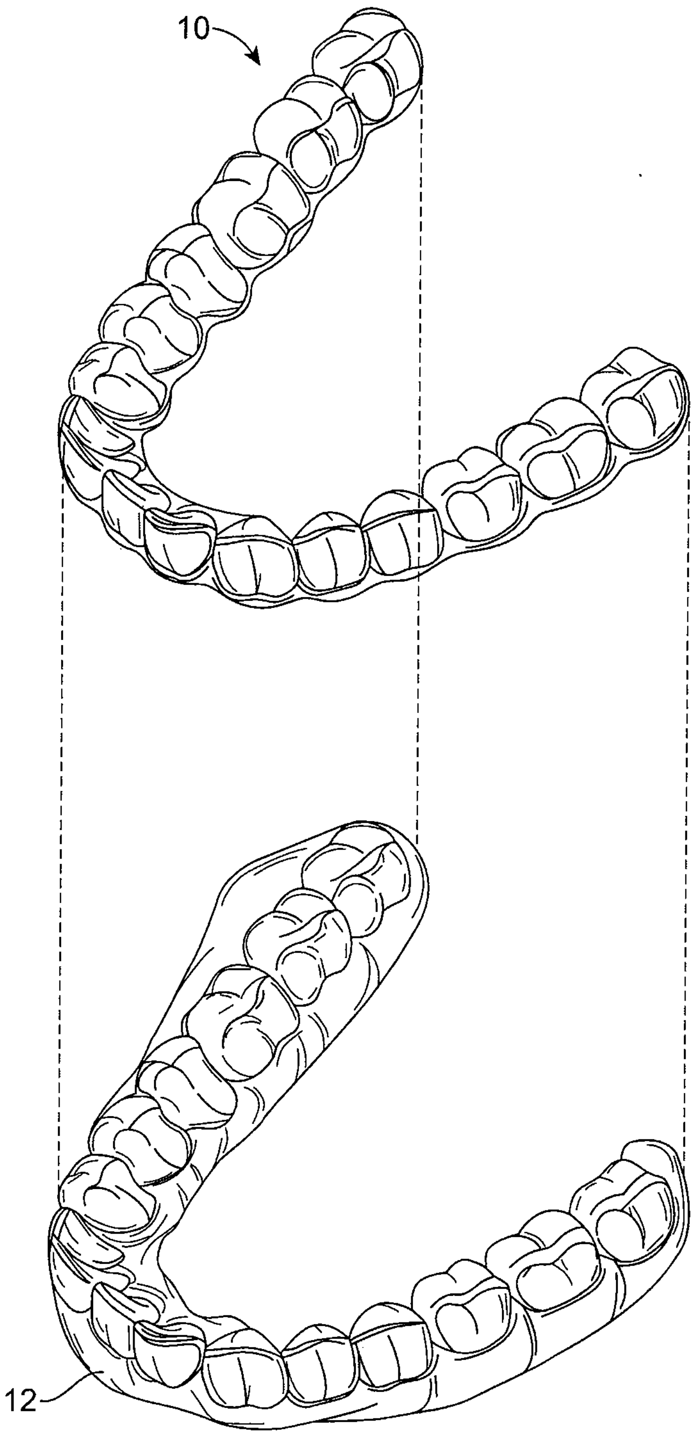
FIG. 1 illustrates a jaw together with an incremental positioning adjustment appliance according to an embodiment of the present invention.

The present invention provides improved systems and methods of managing delivery of an orthodontic treatment plan using treatment guidelines, instructions and appointment planning tools customized to the individual patient being treated. The systems and methods of the present invention include generating a treatment plan for a patient and additionally producing one or more sets of treatment guidelines specifically customized to the patient being treated. The customized treatment guidelines are designed to be provided to a dental practitioner in order to provide enhanced instruction and guidance for delivering the orthodontic treatment to the patient. By customizing the guidelines to the specific patient, the present invention advantageously assists certain practitioners, including those that may lack experience and/or confidence in delivering orthodontic treatment or may be concerned about an ability to achieve a predictable or desired outcome in orthodontic care, and additionally enhances treatment efficacy.

Systems and methods of managing delivery of an orthodontic treatment plan using treatment guidelines, instructions and appointment planning tools customized to the individual patient according to the present invention can be included in a variety of orthodontic treatment regimens. For example, the customized instructions and appointment planning tools can be optionally included and incorporated into other aspects of treatment according to the Invisalign® System. Treatment can be pre-planned for administering to a patient in a series of one or more phases, with at least some of the phases each including a set of appliances that are worn successively by the patient to reposition the teeth through planned arrangements and eventually toward a selected final arrangement. As treatment will typically be planned as a series of treatment phases, the planned phases can each include customized treatment guidelines tailored to that particular phase, which are useful in helping manage delivery and treatment of the patient with the set of appliances. In this way, customized appointment planning and instruction according to the present invention can be integrated with the orthodontic treatment process for improved treatment delivery and/or efficacy.

As set forth above, customized set of treatment guidelines can be provided to the practitioner and designed to correspond to a particular phase of the treatment plan, which can include a corresponding set of appliances that are administered to the patient. Along with the set(s) of appliances that provided to the treating practitioner according to a treatment phase, the practitioner will receive a copy of a customized set of treatment guidelines that will identify all the recommended and/or necessary appointments as well as corresponding instructions or tasks to be completed at each of the appointments. The particular appointments, general or specific timing of the appointments, as well as specific tasks that should be performed at each appointment are customized to the individual patient and typically account for patient-specific factors such as the positioning of the patient's teeth, desired movements, treatment goals, and other clinical considerations.

The present system and methods can by used along with any orthodontic treatment methodology, including patient removable appliances as well as fixed appliances such as more traditional orthodontic brackets and wires, and can even include other dental treatments. More typically, systems and methods of the present invention will be used in conjunction with patient removable, incremental adjustment appliances. FIG. 1 shows one adjustment appliance 10 which is worn by the patient in order to achieve an incremental repositioning of individual teeth in the jaw 12 as described generally above. The appliance can include a shell (e.g., polymeric shell) having teeth-receiving cavities that receive and resiliently reposition the teeth. Such appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com").

As set forth in the prior applications, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance for a set period of time or until the pressure of each appliance on the teeth is minimal or can no longer be felt. A plurality of different appliances (e.g., set) can be designed and even fabricated prior to the patient wearing any appliance of the plurality. At that point, the patient replaces the current adjustment appliance with the next adjustment appliance in the series until no more appliances remain. The appliances are generally not affixed to the teeth so as to require removal by a practitioner (e.g., patient removable) and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such overcorrection may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 2:
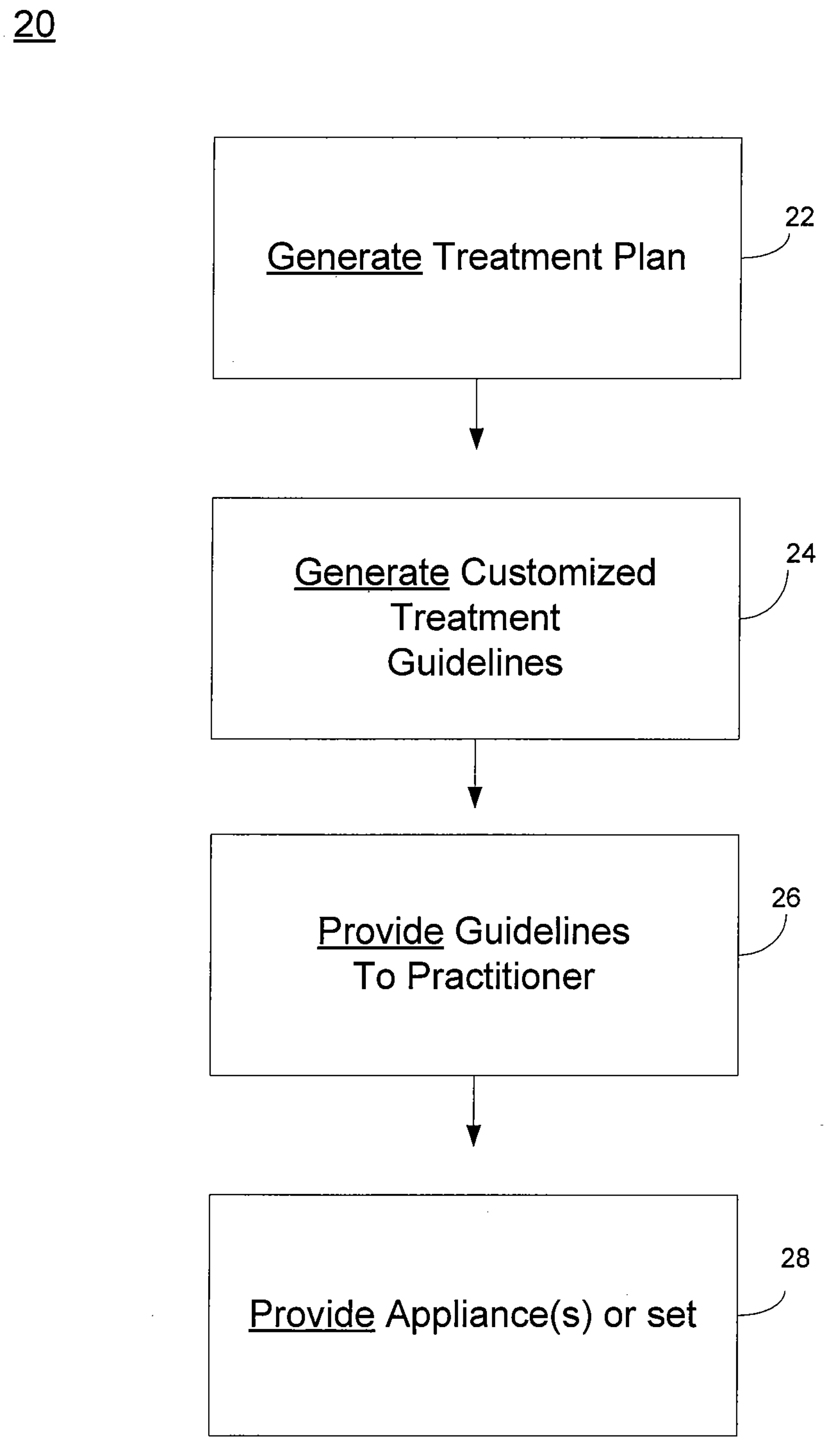
FIG. 2 includes a flow chart illustrating managing delivery of an orthodontic treatment plan including customized treatment guidelines according to an embodiment of the present invention.

Referring to FIG. 2, a process 20 according to the present invention is illustrated. Individual aspects of the process are discussed in further detail below. The process includes generating a treatment plan for repositioning a patient's teeth (Step 22). Briefly, a treatment plan will include obtaining data comprising an initial arrangement of the patient's teeth, which typically includes obtaining an impression or scan of the patient's teeth prior to the onset or start of treatment. The treatment plan will also include identifying a desired final arrangement of the patients teeth, as well as a plurality of planned successive or intermediary tooth arrangements for moving the teeth along a treatment path from the initial arrangement toward the selected final arrangement. As noted, treatment can be pre-planned for administration to a patient in a series of one or more treatment phases, with a phase including a set of appliances that are worn successively by the patient to reposition the teeth through planned arrangements and eventually toward a selected final arrangement. The process further includes proactively generating customized treatment guidelines (Step 24), which can be subsequently provided to the practitioner (Step 26). The treatment plan includes multiple phases of treatment, with a customized set of treatment guidelines generated that correspond to a phase of the treatment plan. The guidelines will include detailed information on timing and/or content (e.g., specific tasks) to be completed during a given phase of treatment, and will be of sufficient detail to guide a less experienced practitioner, or practitioner relatively new to the particular orthodontic treatment process, through the phase of treatment. The process further includes providing or delivering the customized treatment guidelines to the practitioner (Step 26) so as to help instruct the practitioner as how to deliver a given phase of treatment. As set forth above, appliances can be generated based on the planned arrangements and will be provided to the practitioner and ultimately administered to the patient (Step 28). The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of treatment guidelines, or appliances and guidelines can be provided separately.

Figure 3:
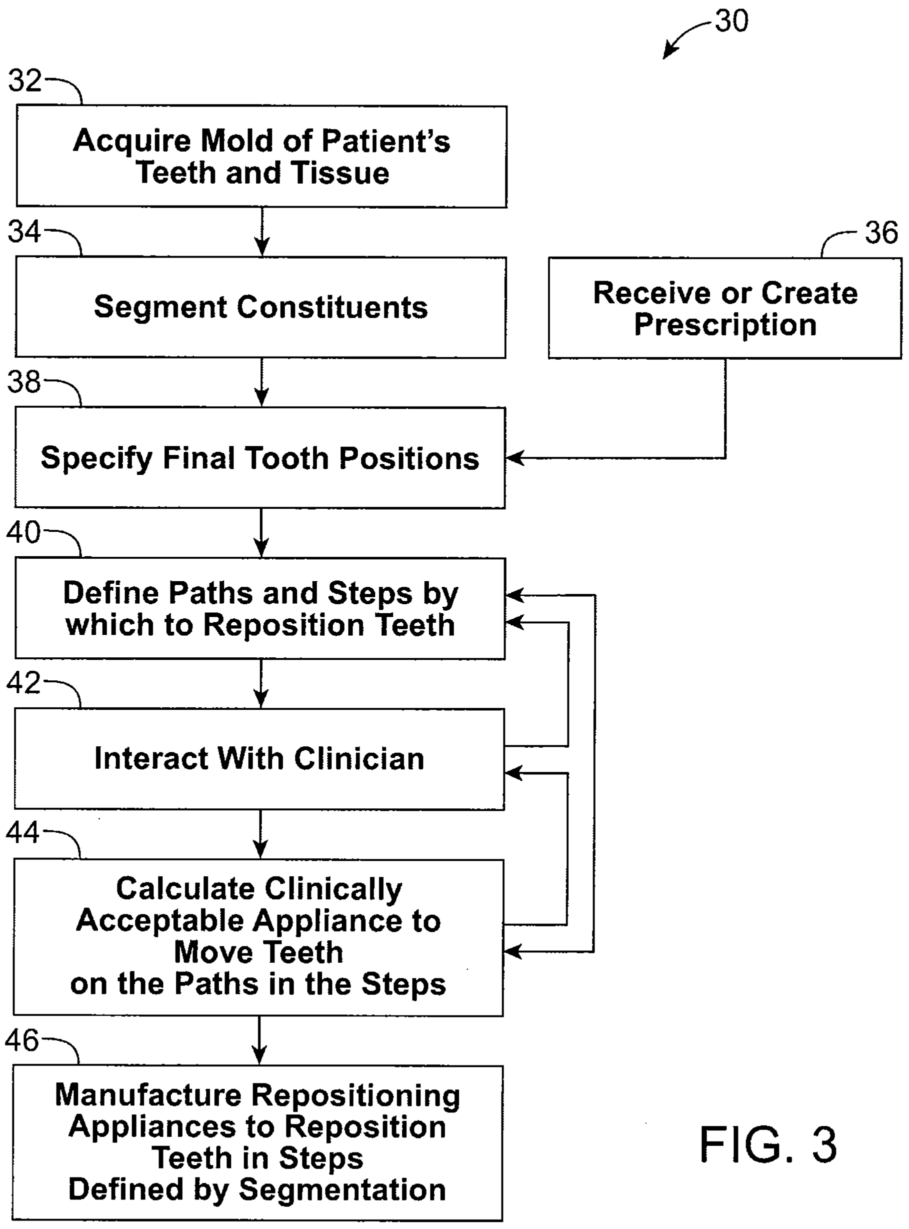
FIG. 3 shows generating a treatment plan according to an embodiment of the present invention.

FIG. 3 illustrates the general flow of an exemplary process 30 for defining and generating a treatment plan, including repositioning appliances for orthodontic treatment of a patient. The steps of the process can be implemented as computer program modules for execution on one or more computer systems.

As an initial step, a mold or a scan of patient's teeth or mouth tissue is acquired (Step 32). This generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents an initial (e.g., pretreatment) arrangement of the patient's teeth and other tissues.

The initial digital data set, which may include both raw data from scanning operations and data representing surface models derived from the raw data, is processed to segment the tissue constituents from each other (Step 34), including defining discrete dental objects. For example, data structures that digitally represent individual tooth crowns can be produced. In some embodiments, digital models of entire teeth are produced, including measured or extrapolated hidden surfaces and root structures.

Desired final position of the teeth, or tooth positions that are desired and/or intended end result of orthodontic treatment, can be received, e.g., from a clinician in the form of a prescription, can be calculated from basic orthodontic principles, or can be extrapolated computationally from a clinical prescription (Step 36). With a specification of the desired final positions of the teeth and a digital representation of the teeth themselves, the final position and surface geometry of each tooth can be specified (Step 38) to form a complete model of the teeth at the desired end of treatment. The result of this step is a set of digital data structures that represents a desired and/or orthodontically correct repositioning of the modeled teeth relative to presumed-stable tissue. The teeth and tissue are both represented as digital data.

Having both a beginning position and a final position for each tooth, the process next defines a treatment path or tooth path for the motion of each tooth (Step 40). This includes defining a plurality of planned successive tooth arrangements for moving teeth along a treatment path from an initial arrangement to a selected final arrangement. In one embodiment, the tooth paths are optimized in the aggregate so that the teeth are moved in the most efficient and clinically acceptable fashion to bring the teeth from their initial positions to their desired final positions.

At various stages of the process, the process can include interact with a clinician responsible for the treatment of the patient (Step 42). Clinician interaction can be implemented using a client process programmed to receive tooth positions and models, as well as path information from a server computer or process in which other steps of process 300 are implemented. The client process is advantageously programmed to allow the clinician to display an animation of the positions and paths and to allow the clinician to reset the final positions of one or more of the teeth and to specify constraints to be applied to the segmented paths.

The tooth paths and associated tooth position data are used to calculate clinically acceptable appliance configurations (or successive changes in appliance configuration) that will move the teeth on the defined treatment path in the steps specified (Step 44). Each appliance configuration corresponds to a planned successive arrangement of the teeth, and represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with other steps, this calculation step can include interactions with the clinician (Step 42).

Having calculated appliance definitions, the process 30 can proceed to the manufacturing step (Step 46) in which appliances defined by the process are manufactured, or electronic or printed information is produced that can be used by a manual or automated process to define appliance configurations or changes to appliance configurations. Appliances according to the treatment plan can be produced in entirety, such that each of the appliances are manufactured (e.g., prior to treatment), or can be manufactured in sets or batches. For example, in some cases it might be appropriate to manufacture an initial set of appliances at the outset of treatment with the intention of manufacturing additional sets of appliances (e.g., second, third, fourth, etc.) after treatment has begun (e.g., as discussed further herein). For example, a first set of appliances can be manufactured and administered to a patient. Following administration, it may be desirable to inspect the progression of the patient's teeth along the treatment path before manufacturing and/or administering subsequent set(s) of appliances.

Generating and/or analyzing digital treatment plans, as discussed herein, can include, for example, use of 3-dimensional orthodontic treatment planning tools such as ClinCheck® from Align Technology, Inc. or other software available from eModels and OrthoCAD, among others. These technologies allow the clinician to use the actual patient's dentition as a starting point for customizing the treatment plan. The ClinCheck® technology uses a patient-specific digital model to plot a treatment plan, and then uses a processed (e.g., segmented) scan of the achieved treatment outcome to assess the degree of success of the outcome as compared to the original digital treatment plan as, as discussed in U.S. Pat. Nos. 7,156,661 and 7,077,647 (see also, below).

As set forth above, once a treatment plan is in place the present invention includes generating customized treatment guidelines that can be provided to the dental practitioner for facilitating administration of treatment and improving desired treatment outcomes. Since the treatment plan typically includes a series of one or more treatment phases, a customized set of treatment guidelines will be generated and will typically include a set of guidelines corresponding to each phase of the treatment plan. Treatment guidelines are provided to the practitioner for administration of treatment to the patient. Since a phase(s) of treatment can include a set of appliances to be administered to the patient, treatment guidelines can be provided to the practitioner concurrently with a set of appliances, or appliances and guidelines can be provided separately. Guidelines can include, for example, hard copies (e.g., paper copies) printed and shipped to the practitioner, or can include one or more electronic copies transmitted to the practitioner over a network, for example, by email or by incorporation into other network-based treatment planning tools (e.g., ClinCheck®).

As a treatment plan will typically include a series of one or more appointments, guidelines will typically include one or more recommended patient/practitioner appointments that may include suggested timing for the appointments. Suggested timing can be specific and may more particularly identify a date or specific date range for scheduling one or more appointments, or can be more generalized and for each appointment may list a broader timing range (e.g., 1 week appointment, 2 week, 3 week, etc.). Appointment timing can be identified to coincide with another treatment event, such as administering an appliance or set of appliance, or wearing of an appliance(s) by the patient for a period of time. Guidelines corresponding to a particular appointment can include a list of recommended tasks to be completed during the practitioner's appointment with the patient. Non-exclusive examples of general tasks that may need to be performed at a given appointment can include appliance delivery and administration to the patient; tooth modifications such as extractions, interproximal reduction (IPR), periodontal evaluation, and the like; placement/removal of attachment(s); auxiliary placement; general monitoring and compliance; treatment progress tracking; finishing appointment or finalization of treatment (e.g., refinement evaluation or final impression and/or order retainer); retainer administration to the patient; retainer maintenance; cleaning appointments; etc. Since the guidelines provided to the practitioner will be specifically customized to the individual patient, the guidelines will not only include identification of the tasks to be completed but will typically include specific details and/or instructions, customized to the individual patient, that will help guide the practitioner through the identified tasks during an appointment with the patient. In some instances, the information provided in the customized guidelines can be further tailored to the practitioner to provide the appropriate level of detail, content, and the like. For example, information provided to the practitioner, such as amount of detail in the identified tasks, can be selected based on the experience level of the practitioner or preferences of the practitioner, e.g., including preferences specified by the practitioner.

As set forth above, guidelines can include, for example, hard copies (e.g., paper copies) printed and shipped to the practitioner, or can include one or more electronic copies transmitted to the practitioner over a network. In addition to recommended appointments, recommended tasks, and specific instructions or guidance on how tasks may be completed, guidelines according to the present invention can include additional information and/or details that can further facilitate a practitioner in administering treatment to the patient, such as support contact information, direction to additional training materials, product ordering information, and the like. For example, where guidelines are provided electronically, such as on-line, additional materials can include one or more hyperlinks, such as JIT troubleshooting links, support links and/or numbers, e-mail links, order placement links, links to ClinCheck sharing modules, training modules or information, etc.

Figure 4:
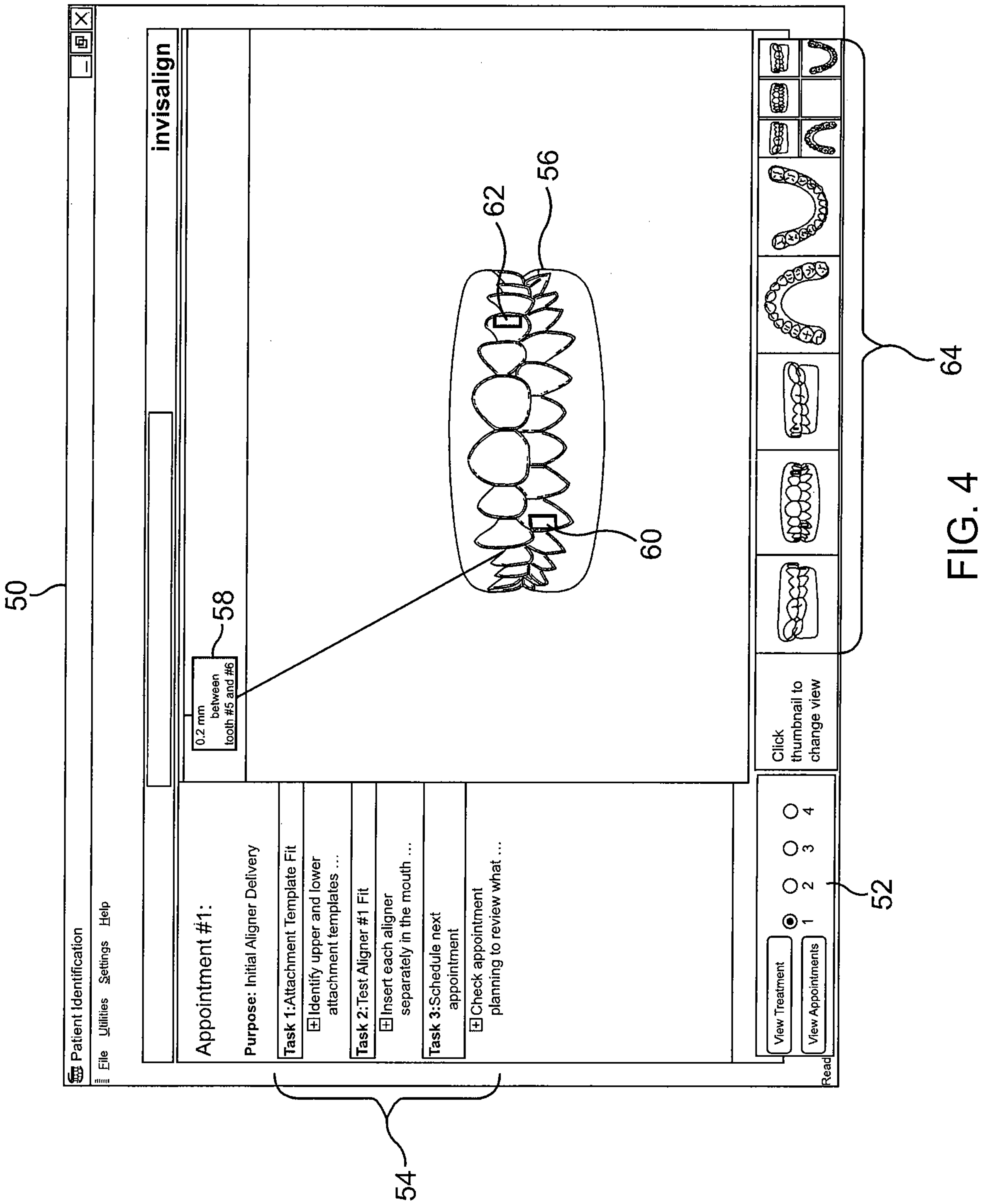
FIG. 4 is a screen shot illustrating a graphical representation of electronically provided guidelines corresponding to a treatment plan according to an embodiment of the present invention.

FIG. 4 shows a screen shot 50 illustrating a graphical representation of electronically provided guidelines corresponding to a treatment plan according to an embodiment of the present invention. A user can select a given appointment (example "Appointment #1" is illustrated) from an appointment menu 52 and customized set of treatment guidelines 54 are displayed corresponding to the selected appointment. The guidelines 54 can include a general description of the selected appointment (e.g., "purpose") so as to communicate to the practitioner general goals to be accomplished at the appointment. The guidelines 54 can further include a list of specific tasks to be completed. Specific tasks can be selected by the practitioner for further viewing of more specific details, such as by selecting a drop down menu that provides more detailed and specific instructions to guide the practitioner through administration of the tasks. For a given appointment, a graphical representation of the patient's projected arrangement of teeth 56 at a given appointment/time can be provided and incorporated into the interface for delivering the guidelines or task instructions. For example, as shown, specific identification 58 of interproximal reduction areas may be shown and can contain details on the reduction to be performed. Attachment locations 60, 62 can also be illustrated on the representation 56 to facilitate treatment administration. Additional views 64 (e.g., thumbnail views) of the patients teeth can also be provided for selection by the practitioner. Providing the guidelines and instructions along with such graphical illustrations can advantageously help to more effectively communicate task instructions to the practitioner at the appropriate treatment time and more effectively manage treatment.

Figure 5A:
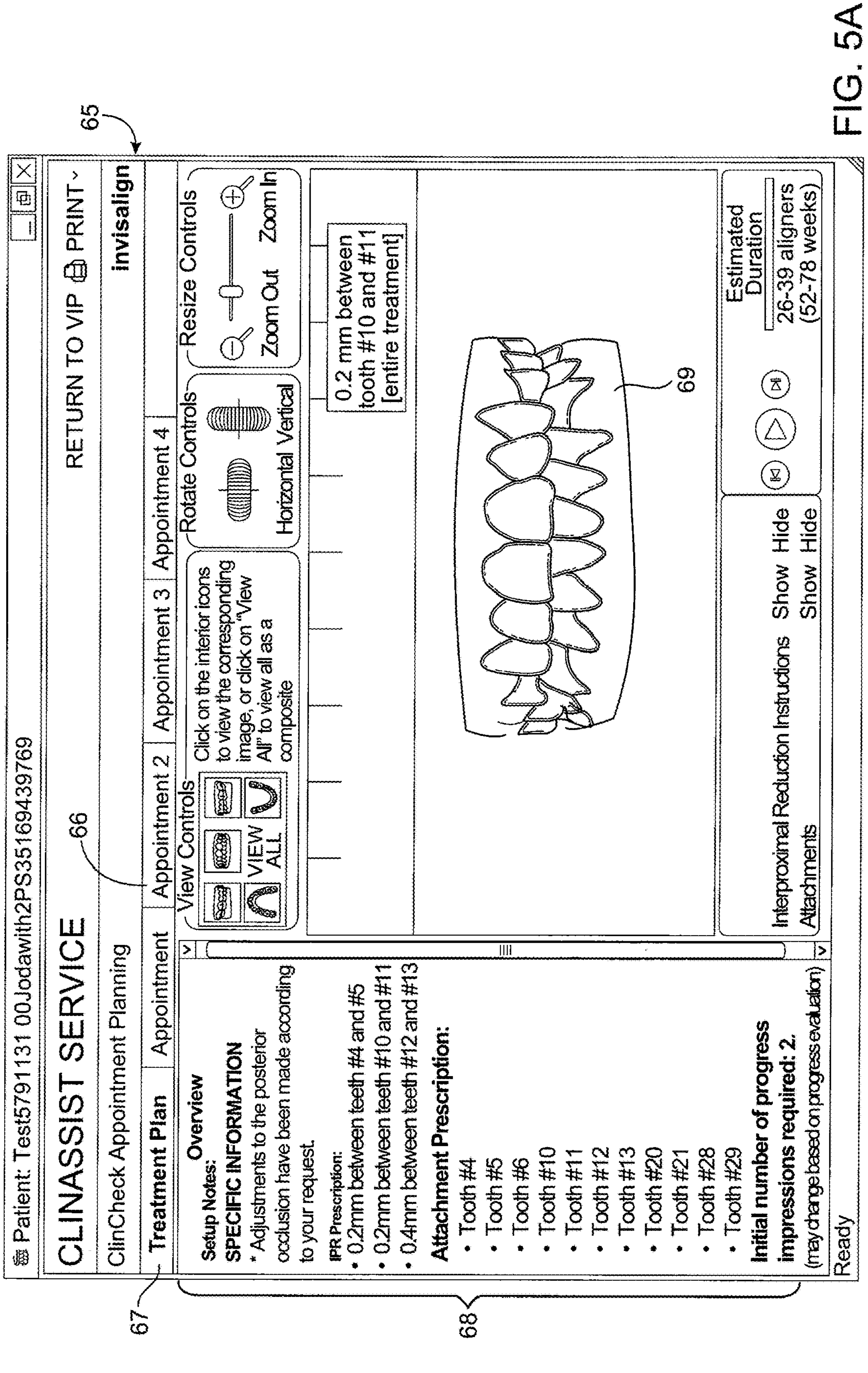
FIG. 5A is a screen shot showing a graphical representation of electronically provided guidelines according to another embodiment of the present invention.

FIG. 5A shows a screen shot 65 illustrating a graphical representation of electronically provided guidelines according to another embodiment of the present invention. As above, a user can select a given appointment (e.g., "Appointment 1", "Appointment 2", etc.) from an appointment menu 66 (e.g., appointment menu bar) for viewing of information including customized guidelines corresponding to the selected appointment. Additionally, the appointment menu 66 can include an option to select an overview or general information on the treatment plan in general, which can be graphically represented as a treatment plan overview tab 67 in the menu 66. Selection of the overview 67 can further display overview information 68 providing information on the treatment plan in general. Information 68 can include, for example, a list of tasks to be completed throughout the treatment (or portion thereof) of the patient. Specifically identified task may be linked to other files so as to provide additional detailed information on a given task upon selection. As above, a graphical representation 69 of the patient's teeth can be presented illustrating projected tooth positions at a given time or appointment.

Figure 5B:
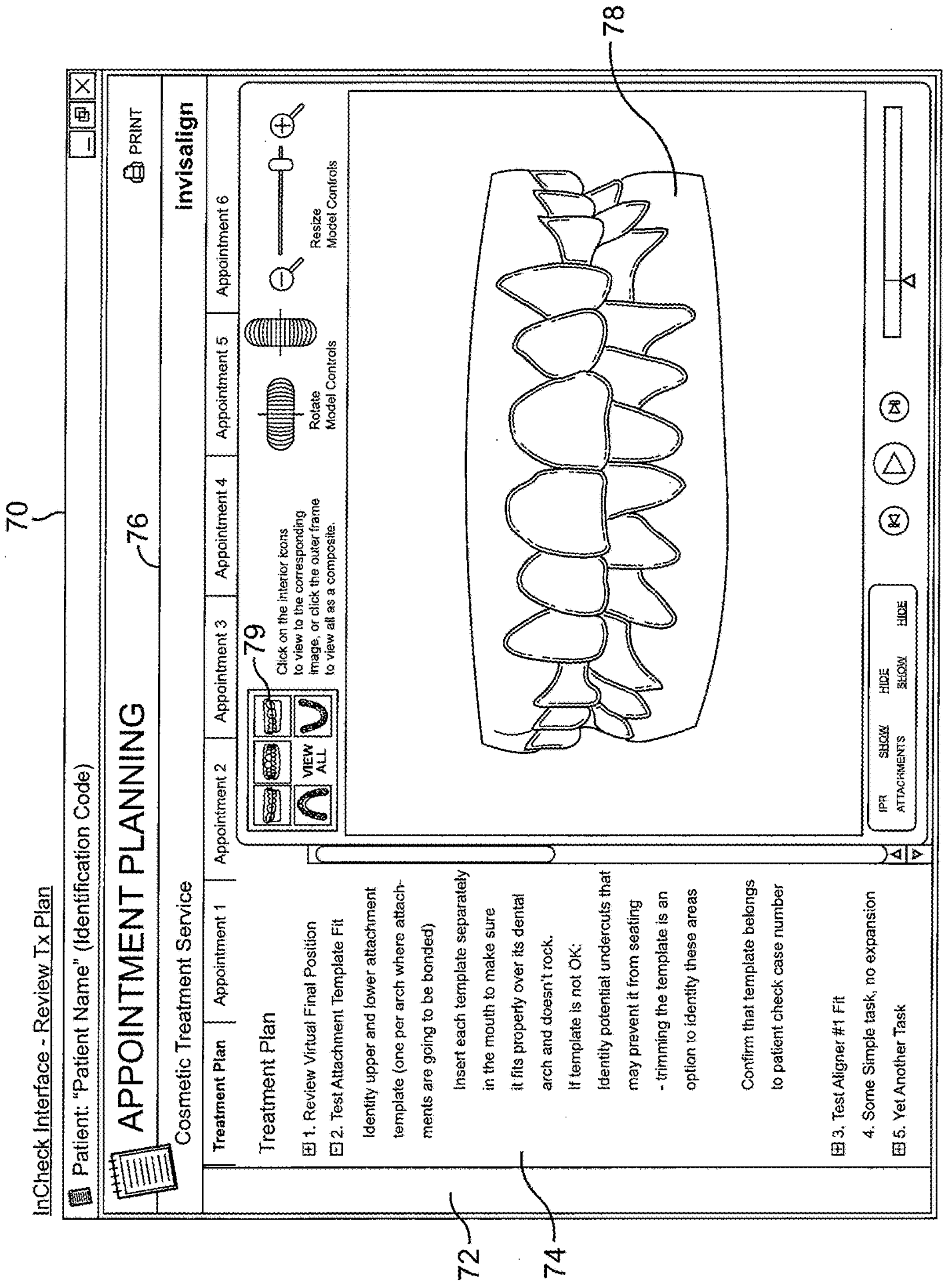
FIG. 5B is a screen shot showing a graphical representation of electronically provided guidelines corresponding to a treatment plan according to another embodiment of the present invention.

FIG. 5B shows a screen shot 70 illustrating a graphical representation of electronically provided guidelines corresponding to a treatment plan according to another embodiment of the present invention. Customized treatment guidelines 72 are shown provided according to the treatment plan. As above, drop down options 74 are provided that allow the practitioner to select a given task in order to view more detailed instructions and information for guidance on how to administer the task. The practitioner can toggle between various appointments by using an appointment menu 76 (e.g., menu bar), where a given appointment according to the treatment plan can be selected, thereby providing a list of corresponding tasks to be completed at the selected appointment. Additionally, a graphical representation 78 of the patient's projected tooth arrangement at a given appointment or time can be displayed and may include a view menu 79 for selecting different graphical views of the patients teeth. Additional animation and/or instructions can be included or incorporated into a graphical representation of the patient's teeth to further communicate treatment guidelines and tasks.

Figure 6:
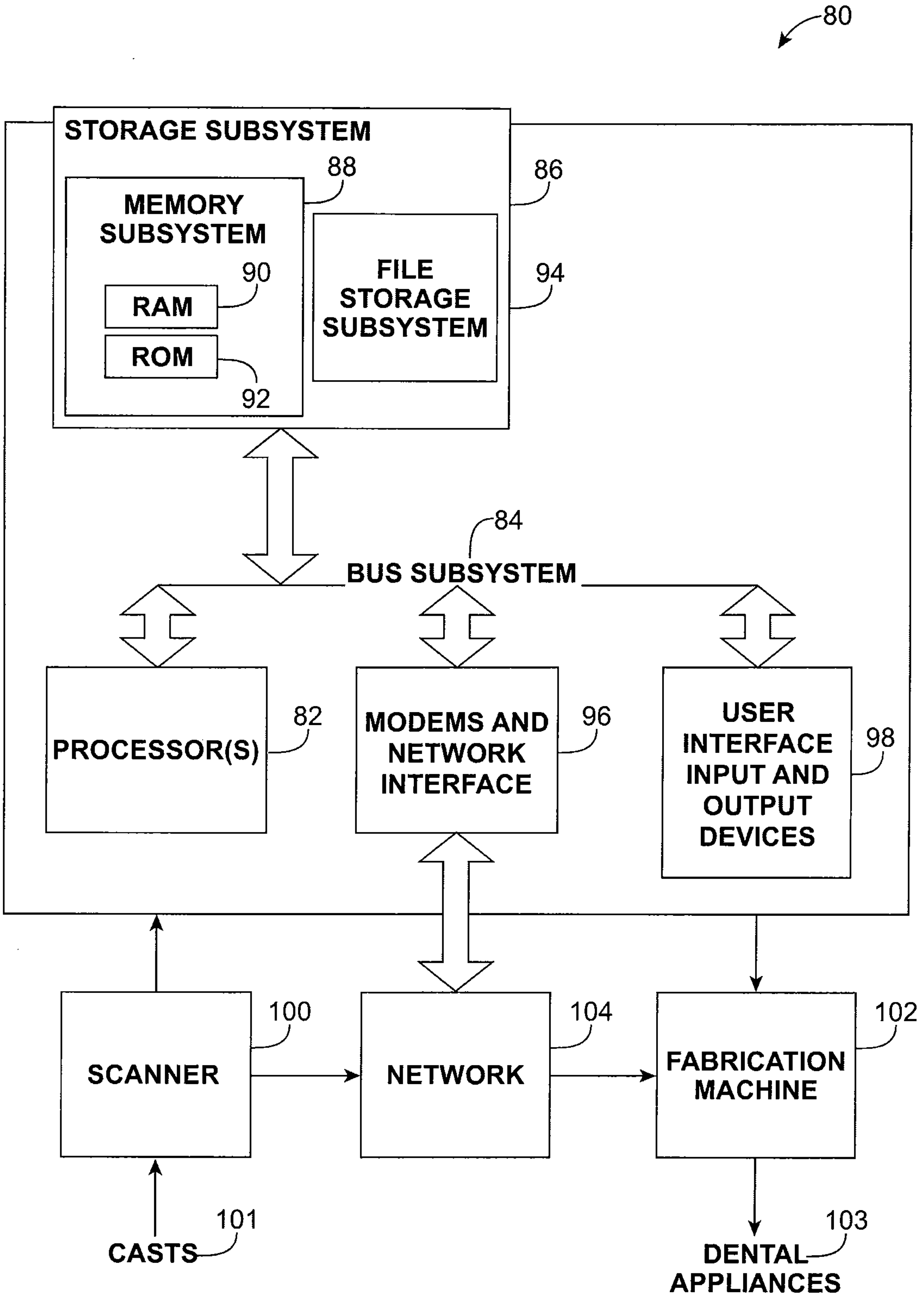
FIG. 6 is a block diagram illustrating a system for generating appliances in accordance with methods and processes of the present invention.

FIG. 6 is a simplified block diagram of a data processing system 80 that may be used in executing methods and processes described herein. The data processing system 80 typically includes at least one processor 82 that communicates with a number of peripheral devices via bus subsystem 84. These peripheral devices typically include a storage subsystem 86 (memory subsystem 88 and file storage subsystem 94), a set of user interface input and output devices 98, and an interface to outside networks 96, including the public switched telephone network. This interface is shown schematically as "Modems and Network Interface" block 96, and is coupled to corresponding interface devices in other data processing systems via communication network interface 104. Data processing system 80 can include, for example, one or more computers, such as a personal computer, workstation, mainframe, and the like.

The user interface input devices 98 are not limited to any particular device, and can typically include, for example, a keyboard, pointing device, mouse, scanner, interactive displays, etc. Similarly, various user interface output devices can be employed in a system of the invention, and can include, for example, one or more of a printer, display (e.g., visual, non-visual) system/subsystem, controller, projection device, audio output, and the like.

Storage subsystem 86 maintains the basic required programming, including computer readable media having instructions (e.g., operating instructions, etc.), and data constructs. The program modules discussed herein are typically stored in storage subsystem 86. Storage subsystem 86 typically comprises memory subsystem 88 and file storage subsystem 94. Memory subsystem 88 typically includes a number of memories (e.g., RAM 90, ROM 92, etc.) including computer readable memory for storage of fixed instructions, instructions and data during program execution, basic input/output system, etc. File storage subsystem 94 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the Internet's World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 100 includes any means for obtaining an image of a patient's teeth, some of which have been described herein above, which can be obtained either from the patient or from treating professional, such as an orthodontist, and includes means of providing the image data/information to data processing system 80 for further processing. In some embodiments, scanner 100 may be located at a location remote with respect to other components of the system and can communicate image data and/or information to data processing system 80, for example, via a network interface 104. Fabrication system 102 fabricates dental appliances based on a treatment plan, including data set information received from data processing system 80. Fabrication machine 102 can, for example, be located at a remote location and receive data set information from data processing system 80 via network interface 104.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A computer-implemented method for managing delivery of a dental treatment plan, the method comprising:

identifying an dental treatment plan for a patient's teeth;

generating one or more first treatment tasks to implement a first phase of the dental treatment plan;

obtaining a digital representation of a dentition;

generating graphical treatment instructions representing how to administer the one or more first treatment tasks on the digital representation of the dentition; and prior to fabricating a first dental appliance for carrying out the dental treatment plan, graphically representing, to a treating practitioner, the graphical treatment instructions for how to administer the one or more first treatment tasks.

2. The computer-implemented method of claim 1, further comprising:

determining, using the digital representation, whether or not the patient's teeth accord with one or more customized treatment guidelines for the patient's teeth;

identifying, based on a determination whether or not the patient's teeth accords with the one or more customized treatment guidelines, one or more second tasks for administering a second phase of the dental treatment plan to the patient's teeth.

3. The computer-implemented method of claim 1, further comprising providing instructions to administer the first dental appliance before the first phase.

4. The computer-implemented method of claim 2, wherein the one or more first tasks comprise:

determining whether the patient's teeth are progressing according to the first phase of the dental treatment plan; and identifying, based on determining whether the patient's teeth are progressing according to the first phase, a second batch of orthodontic appliances to implement the second phase of the dental treatment plan.

5. The computer-implemented method of claim 2, wherein:

the one or more first tasks comprise:

determining whether the patient's teeth are progressing according to the first phase of the dental treatment plan, and identifying, based on determining whether the patient's teeth are progressing according to the first phase, a second batch of orthodontic appliances to implement the second phase of the dental treatment plan, and further comprising:

providing instructions to administer the first dental appliance before a beginning of the first phase; and providing instructions to administer the second batch of the orthodontic appliances after the beginning of the first phase.

6. The computer-implemented method of claim 2, further comprising graphically representing the one or more customized treatment guidelines, the one or more first tasks, or some combination thereof, to a user of a computing device.

7. The computer-implemented method of claim 6, further comprising graphically representing an appointment menu displaying appointment information relevant to an appointment, the appointment information comprising at least a portion of the one or more customized treatment guidelines, the one or more first tasks, or some combination thereof.

8. The computer-implemented method of claim 1, further comprising graphically representing an appointment menu displaying appointment information, the appointment information guiding a practitioner to track progress of the dental treatment plan during the first phase.

9. The computer-implemented method of claim 2, further comprising graphically representing an appointment menu displaying appointment information, the appointment information guiding a practitioner to order a second batch of orthodontic appliances to implement the second phase of the dental treatment plan.

10. The computer-implemented method of claim 1, further comprising graphically representing an appointment menu displaying appointment information, the appointment information guiding a practitioner to provide one or more refinements to the dental treatment plan.

11. The computer-implemented method of claim 1, further comprising graphically representing an appointment menu instructing administration of at least a portion of the dental treatment plan for the patient's teeth.

12. The computer-implemented method of claim 1, further comprising graphically representing an appointment menu instructing administration of one or more of: interproximal reduction (IPR), attachment placement, attachment removal, or some combination thereof, for the patient's teeth.

13. The computer-implemented method of claim 1, further comprising graphically representing an appointment menu instructing administration of attachment removal in order to perform a refinement of the dental treatment plan.

14. The computer-implemented method of claim 1, further comprising graphically representing an appointment menu providing a future appointment having an appointment timing identified to coincide with a treatment event.

15. The computer-implemented method of claim 1, further comprising graphically representing an appointment menu providing a future appointment having an appointment timing identified to coincide with a treatment event, wherein the treatment event comprises wearing of the first dental appliance for a period of time.

16. The computer-implemented method of claim 1, further comprising graphically representing a list of recommended tasks to be completed during a practitioner's appointment with the patient.

17. The computer-implemented method of claim 1, wherein graphically representing treatment instructions for how to administer the one or more first treatment tasks includes graphical illustrations of a projected position of the patient's teeth during at least a portion of the first phase including annotations of locations for treatment on the graphical illustrations.

18. The computer-implemented method of claim 1, further comprising graphically representing tasks for a plurality of appointments related to the dental treatment plan.

19. The computer-implemented method of claim 1, wherein obtaining a digital representation of the patient's teeth during the first phase of the dental treatment plan comprises one or more of: obtaining a scan of the patient's teeth and obtaining a digitization of physical impressions of the patient's teeth.

20. The computer-implemented method of claim 1, further comprising providing the first dental appliance to a treatment professional or to the patient.

* * * * *